(12) United States Patent
Sudo et al.

(10) Patent No.: US 9,816,917 B2
(45) Date of Patent: Nov. 14, 2017

(54) VITREOUS SILICA CRUCIBLE AND DISTORTION-MEASURING APPARATUS FOR THE SAME

(71) Applicant: SUMCO CORPORATION, Minato-ku, Tokyo (JP)

(72) Inventors: Toshiaki Sudo, Akita (JP); Tadahiro Sato, Akita (JP); Ken Kitahara, Akita (JP); Eriko Kitahara, Akita (JP)

(73) Assignee: SUMCO CORPORATION, Tokyo (JP)

( * ) Notice: Subject to any disclaimer, the term of this patent is extended or adjusted under 35 U.S.C. 154(b) by 0 days.

(21) Appl. No.: 15/103,609

(22) PCT Filed: Dec. 25, 2014

(86) PCT No.: PCT/JP2014/084217
§ 371 (c)(1),
(2) Date: Jun. 10, 2016

(87) PCT Pub. No.: WO2015/099001
PCT Pub. Date: Jul. 2, 2015

(65) Prior Publication Data
US 2016/0313234 A1 Oct. 27, 2016

(30) Foreign Application Priority Data

Dec. 28, 2013 (JP) .................. 2013-273686
Dec. 28, 2013 (JP) .................. 2013-273687

(51) Int. Cl.
*C30B 15/10* (2006.01)
*C30B 29/06* (2006.01)
(Continued)

(52) U.S. Cl.
CPC ............... *G01N 21/23* (2013.01); *C03C 3/04* (2013.01); *C30B 15/10* (2013.01); *C30B 29/06* (2013.01);
(Continued)

(58) Field of Classification Search
CPC ........ G01B 11/24; G01N 21/23; C30B 15/10; C30B 29/06; G01L 1/24; C03C 3/04
(Continued)

(56) References Cited

U.S. PATENT DOCUMENTS 6,922,251 B1 * 7/2005 Kirchhoff ................. C21C 5/44
356/601
7,174,787 B2 * 2/2007 Sadri ....................... F27D 19/00
73/597
(Continued)

FOREIGN PATENT DOCUMENTS

JP H06147986 A 5/1994
JP 2000247778 A 9/2000
(Continued)

OTHER PUBLICATIONS

International Search Report (ISR) dated Mar. 17, 2015, issued for International application No. PCT/JP2014/084217.
(Continued)

*Primary Examiner* — Roy M Punnoose
(74) *Attorney, Agent, or Firm* — Law Office of Katsuhiro Arai

(57) ABSTRACT

In an embodiment, a distortion-measuring apparatus for measuring a distortion distribution of an entire vitreous silica crucible in a non-destructive way includes: a light source 11; a first polarizer 12 and a first quarter-wave plate 13 disposed between the light source 11 and an outer surface of a vitreous silica crucible wall; a camera 14 disposed inside of a vitreous silica crucible 1; a camera control mechanism 15 configured to control a photographing direction of the camera 14; a second polarizer 16 and a second quarter-wave plate 17 disposed between the camera 14 and an inner surface of the vitreous silica crucible wall. An
(Continued)

optical axis of the second quarter-wave plate 17 inclines 90 degrees with respect to the first quarter-wave plate 13.

18 Claims, 10 Drawing Sheets

(51) Int. Cl.
*G01N 21/23* (2006.01)
*G01L 1/24* (2006.01)
*G01L 5/00* (2006.01)
*C03C 3/04* (2006.01)
*H04N 5/232* (2006.01)

(52) U.S. Cl.
CPC .............. *G01L 1/24* (2013.01); *G01L 5/0047* (2013.01); *H04N 5/232* (2013.01); *G01N 2201/062* (2013.01); *G01N 2201/0683* (2013.01)

(58) Field of Classification Search
USPC .......................................................... 356/364
See application file for complete search history.

(56) References Cited

U.S. PATENT DOCUMENTS

| 7,665,362 | B2* | 2/2010 | Sadri | F27D 19/00 73/597 |
| 7,924,438 | B2* | 4/2011 | Kleinloh | F27D 21/0021 356/601 |
| 9,279,773 | B2* | 3/2016 | Harvill | G01B 11/303 |
| 2012/0145068 | A1* | 6/2012 | Takanashi | C30B 15/26 117/15 |
| 2013/0120738 | A1* | 5/2013 | Bonin | G01N 25/72 356/72 |
| 2013/0250277 | A1 | 9/2013 | Wang et al. | |
| 2014/0182510 | A1* | 7/2014 | Yamagata | C03C 3/06 117/208 |
| 2014/0326172 | A1 | 11/2014 | Sudo et al. | |
| 2015/0007764 | A1* | 1/2015 | Sudo | C30B 15/10 117/15 |

FOREIGN PATENT DOCUMENTS

| JP | 2001342030 A | 12/2001 |
| JP | 2010280567 A | 12/2010 |
| WO | 2013094318 A1 | 6/2013 |

OTHER PUBLICATIONS

Kishii et al., Glass Kogyo ni Riyo sareru Kodansei Gijutsu, Oyo Kogaku, 2002, pp. 16-20, No. 6.

Toru Kishii, Hizumi Kensaki no Riyo Gijutsu, New Glass Technology, 1982, pp. 44-56, vol. 2, No. 2.

* cited by examiner

[FIG. 1]
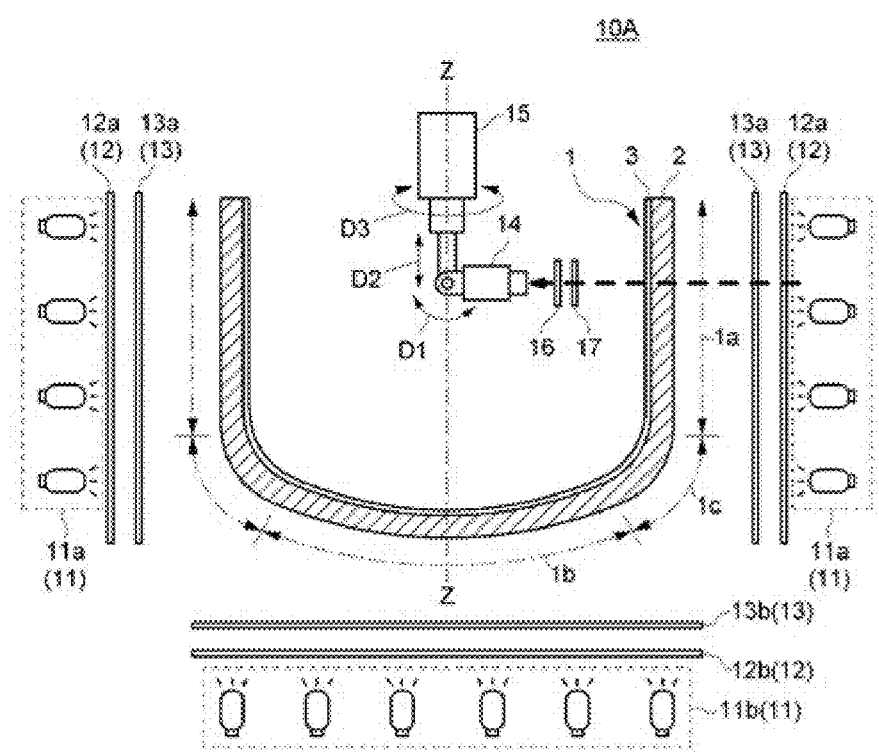

[FIG. 2]
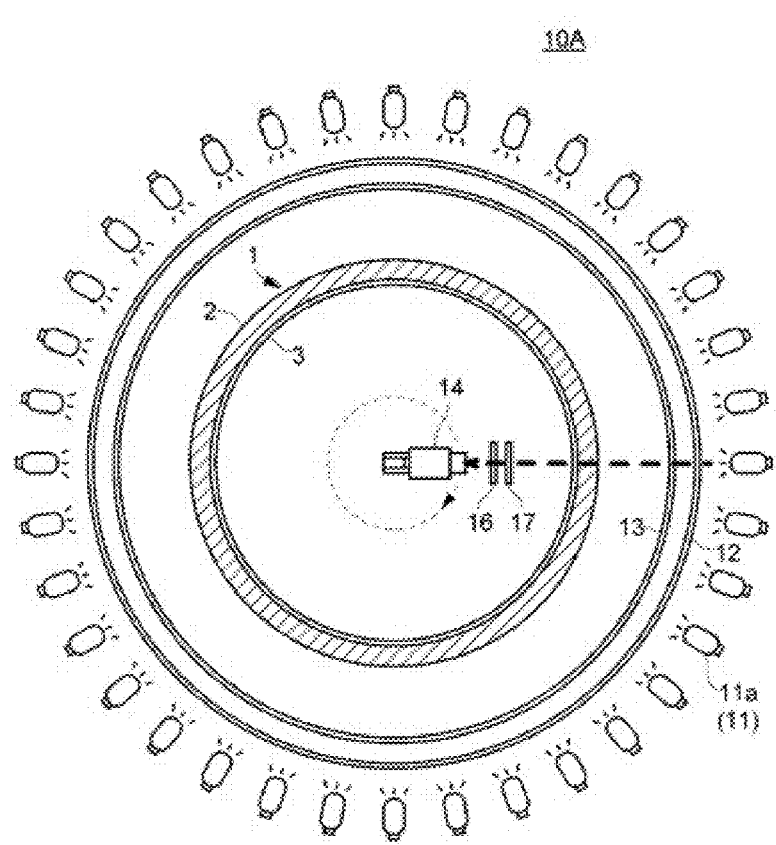

[FIG. 3]
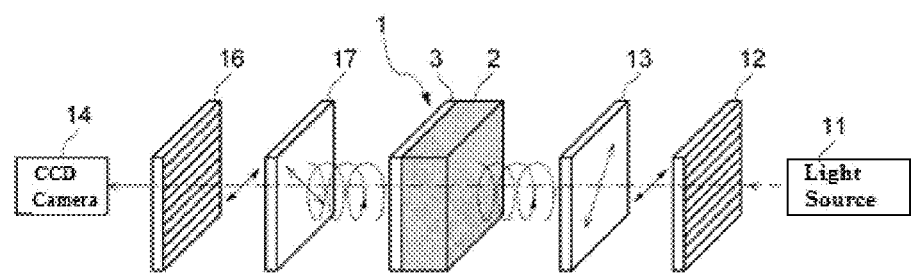

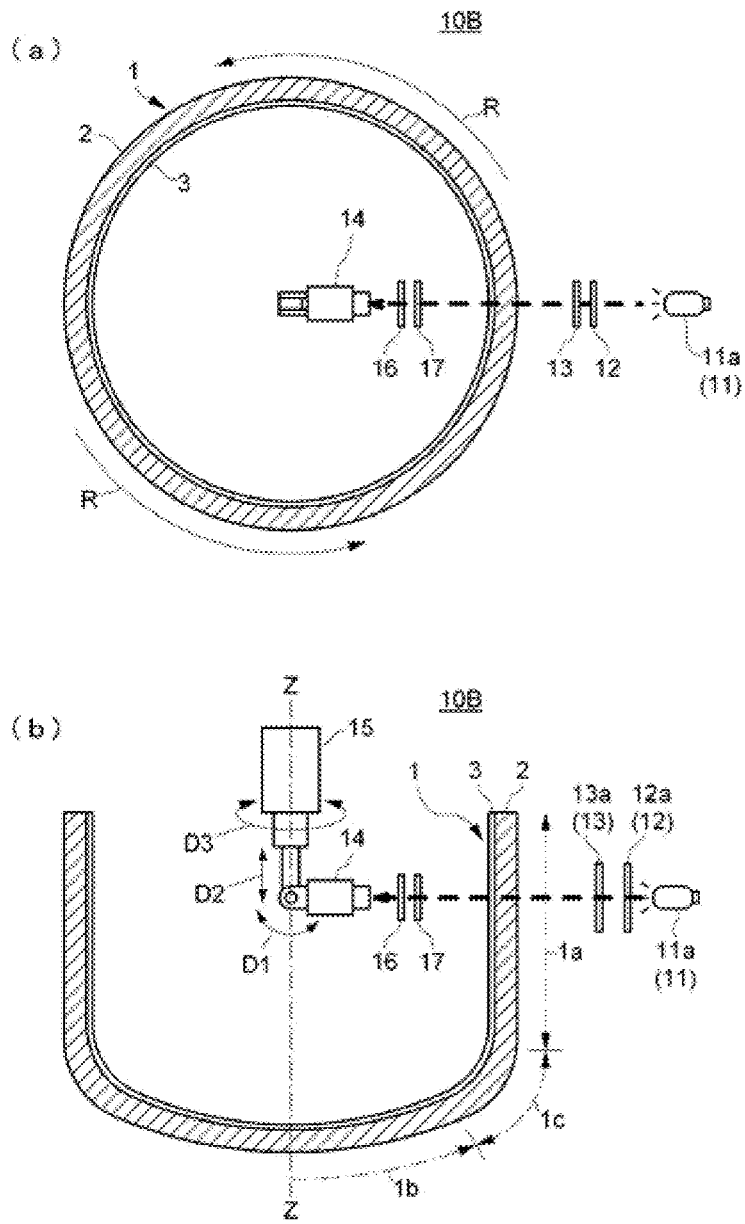
[FIG. 4]

[FIG. 5]
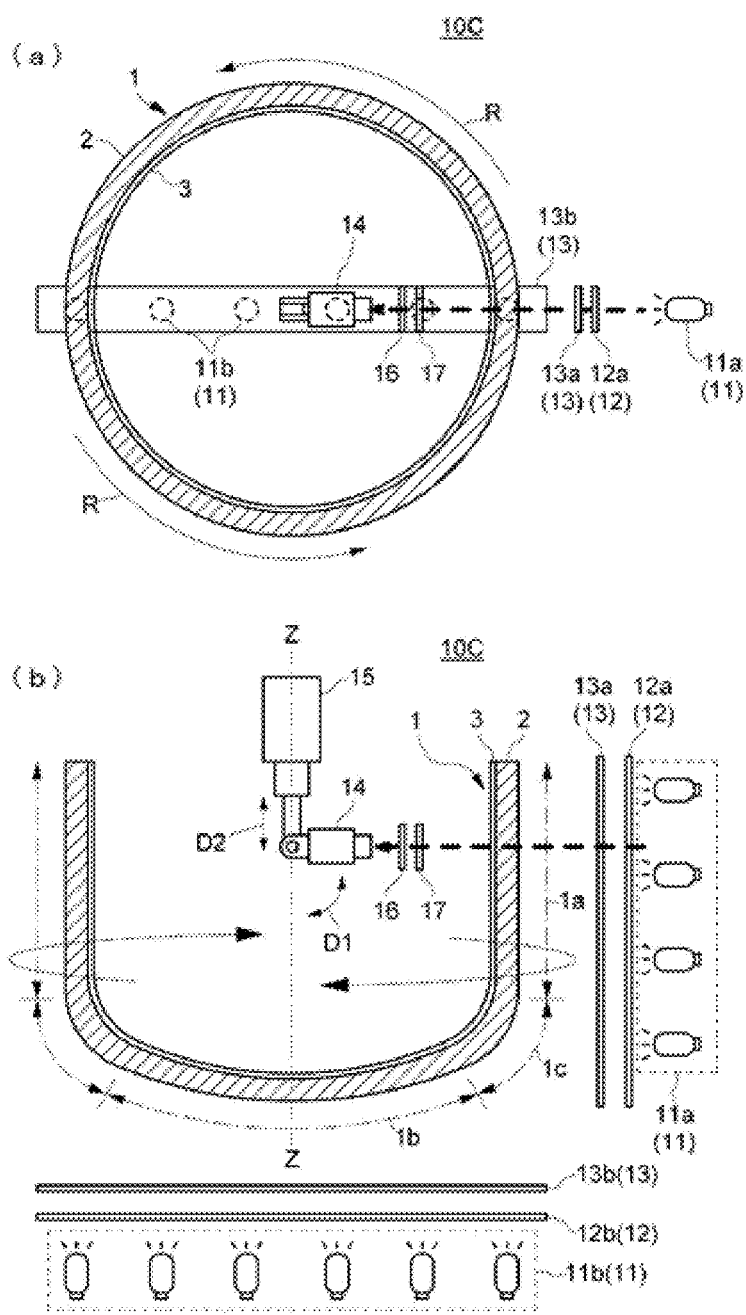

[FIG. 6]
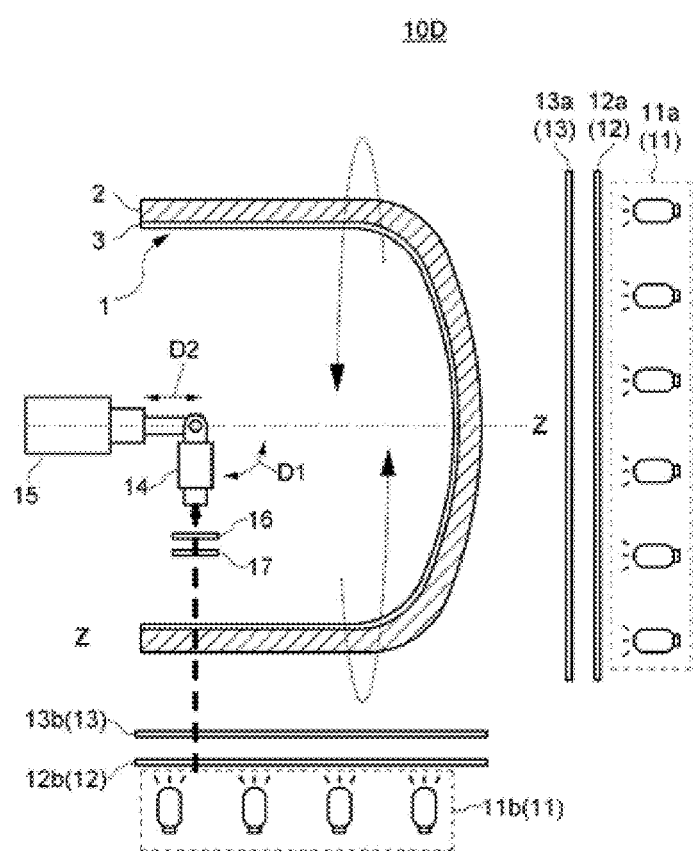

[FIG. 7]
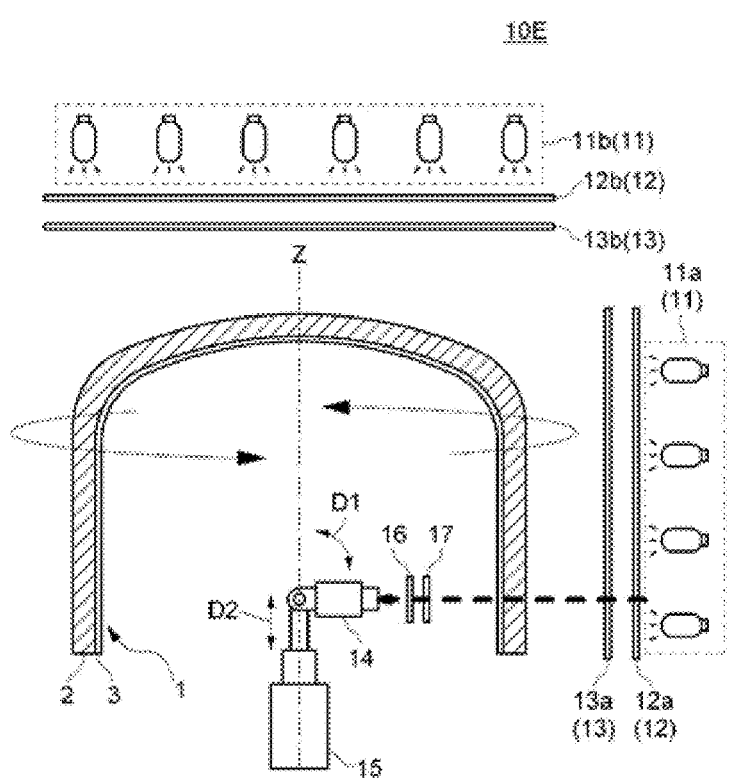

[FIG. 8]
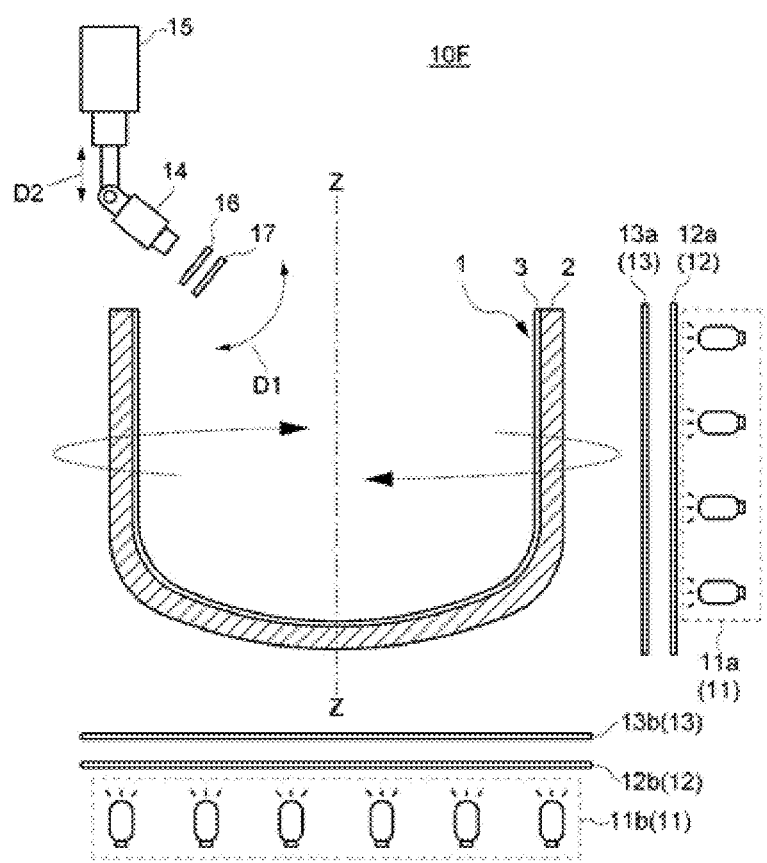

[FIG. 9]
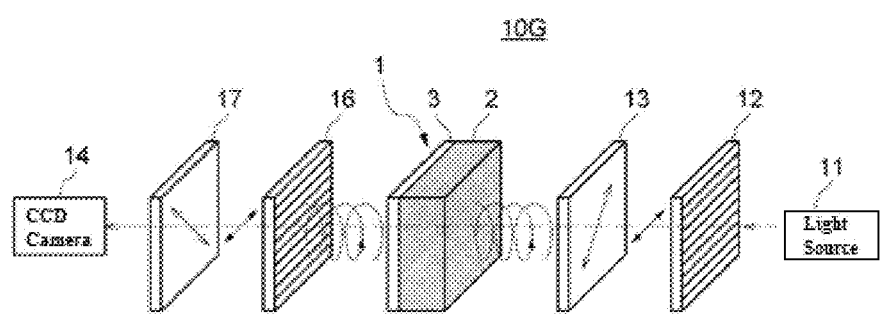

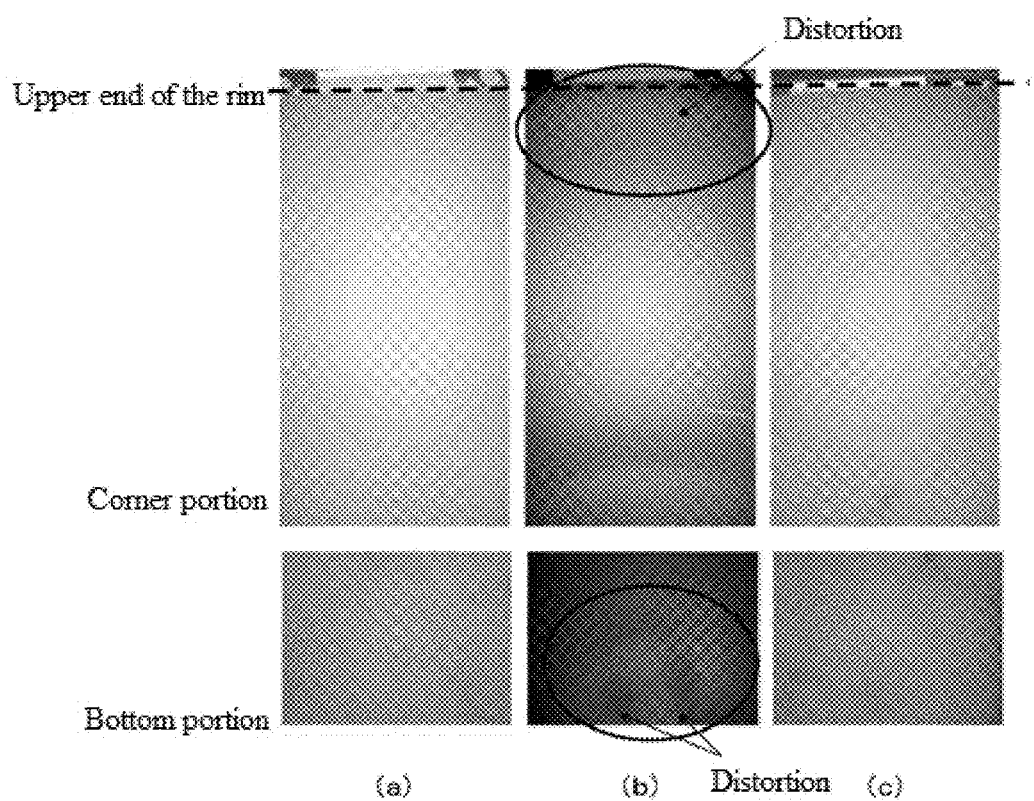
[FIG. 10]

VITREOUS SILICA CRUCIBLE AND DISTORTION-MEASURING APPARATUS FOR THE SAME

This application is the U.S. National Phase under 35 U.S.C. §371 of International Application PCT/JP2014/084217, filed Dec. 25, 2014, which claims priority to Japanese Patent Application No. 2013-273686 and 2013-273687, filed Dec. 28, 2013. The International Application was published under PCT Article 21(2) in a language other than English.

TECHNICAL FIELD

The present invention relates to a vitreous silica crucible and a distortion-measuring apparatus of the same, especially relates to a distortion-measuring apparatus for measuring distortion of a vitreous silica crucible for pulling up silicon single crystal in a non-destructive way.

BACKGROUND ART

When manufacturing silicon single crystal by the Czochralski method (CZ method), a vitreous silica crucible is used (for example, see Patent Literature 1). In the CZ method, silicon material is put into the vitreous silica crucible, and thereafter heated and fused. Then, a seed crystal is dipped into this silicon melt. The seed crystal is pulled up gradually while rotating the crucible so as to let the single crystal grow. In order to manufacture high-quality silicon single crystal used for semiconductor devices at low cost, it is necessary to raise the yield of silicon single crystal in one pulling process. For that purpose, it is necessary to use a crucible with large capacity which can contain a large amount of material.

In a preparation step before pulling up silicon single crystal in the CZ method, silicon material is pre-filled into the vitreous silica crucible. Such filling operation is mainly conducted by manpower. This is because the vitreous silica crucible is very fragile and tends to easily have cracking or chipping, and therefore cracks easily when loading a large amount of material vigorously. Also, in order to obtain a silicon single crystal ingot as big as possible in one pulling process, it is necessary to try to tightly fill the crucible with a large amount of material at the beginning. For this purpose, it is necessary to carefully conduct the filling operation by taking into consideration the size and shape of small fragments of polycrystalline silicon or the like.

However, although the filling operation is carefully conducted by manpower, there still may be a phenomenon that the vitreous silica crucible suddenly cracks while filling the crucible with the polycrystalline silicon pieces. This phenomenon is considered to be caused by distortion remaining in the silica glass when manufacturing the vitreous silica crucible. That is to say, it is presumed that, when the polycrystalline silicon pieces are put on a position where the residual distortion is significant, even with a weak shock, the shock would be a trigger to cause the vitreous silica crucible's cracking. The vitreous silica crucible's residual distortion is very obvious especially in an annealed crucible formed by annealing a crucible once completed, and in a so-called re-arc crucible formed by repeating arc fusing of a crucible once completed (see patent Literature 2).

If a vitreous silica crucible has cracked, not only the crucible itself cannot be used, but the entire filling operation to fill the crucible with the material conducted until the cracking will be wasted. This will become a quite big loss on the aspect of costs or man-hours. It is difficult to prevent such cracking completely but it is possible to solve this problem by dealing with it as a defective product or a B-grade product when the distortion remaining in a vitreous silica crucible is big. For this purpose, it is necessary to accurately measure the distribution of distortion remaining in a vitreous silica crucible.

BACKGROUND ART LITERATURE

Patent Literature

Patent Literature 1: Japanese Patent Application Laid-Open 2010-280567
Patent Literature 2: Japanese Patent Application Laid-Open 2001-342030

SUMMARY OF THE INVENTION

Problems to Be Solved by the Invention

Currently, the diameter (opening diameter) of the opening portion of the crucible for pulling a typical single crystal silicon ingot with a large opening diameter is more than 32 inches (about 800 mm). This kind of crucible with such a large opening diameter is used for pulling a single crystal silicon ingot with a diameter of more than 300 mm. The wall thickness of the crucible is more than 10 mm or even more than 20 mm. Normally, the wall thickness of a large-scale crucible in which an opening diameter is more than 32 inches (about 800 mm) is more than 10 mm, and the wall thickness of a large-scale crucible in which an opening diameter is more than 40 inches (about 1000 mm) is more than 13 mm. There is an opaque vitreous silica layer containing a plurality of micro bubbles on the crucible's outer surface side, and there is a transparent vitreous silica layer containing almost no bubbles on the crucible's inner surface side.

The vitreous silica crucible is formed by filling quartz powder into a carbon rotating mold, performing arc fusing to the quartz powder which has been shaped to a crucible shape, performing cooling and vitrification. Therefore, the entire vitreous silica crucible cannot be heated uniformly. As a result, there exists residual distortion in silica glass. The residual distortion represents distribution of glass density. When there is a density difference in transparent glass, there will be a density distribution in the surface perpendicular to the optical axis so that the density distribution can be measured as the residual distortion.

A conventional distortion-measuring instrument can measure the distortion of a thin transparent glass plate but it cannot measure the distortion of a vitreous silica crucible in a non-destructive way. For this reason, a conventional method for measuring the distortion of a vitreous silica crucible is a so-called destructive test, wherein the crucible is cut in a vertical direction and a cross section of the crucible is measured by a distortion-measuring instrument. There is an opaque layer that includes a plurality of micro bubbles and is disposed on the outside of the vitreous silica crucible used for pulling up a silicon single crystal. Therefore, even though an operator tries to optically measure the distortion by using the transmitted light of light irradiated to the crucible's surface, it is impossible to measure the distortion because the opaque layer prevents the light from transmitting.

However, there is considered to be a difference in a distortion state between a sample cut out from a crucible product and the crucible product whose entire circumference is restrained before the sample is cut out. For example, although there is a large distortion remaining in the sample cut out, there can be almost no distortion remaining in the restrained state. Therefore, it is expected to be able to accurately examine what kind of residual distortion is included in a status of crucible product by a non-destructive way.

Therefore, an object of the present invention is to provide a measuring apparatus of a vitreous silica crucible's distortion, which can measure a distortion distribution of the whole vitreous silica crucible in a non-destructive way. Additionally, an another object of the present invention is to provide a vitreous silica crucible which has a designated residual distortion distribution and is not easily broken during filling of material by using a distortion-measuring apparatus to measure in a non-destructive way.

Means for Solving the Problems

In order to solve the above problems, a distortion-measuring apparatus of the present invention is a distortion-measuring apparatus of a vitreous silica crucible which includes: an opaque outer layer enclosing a plurality of bubbles; and a transparent inner layer with bubbles removed. The apparatus includes: a light source disposed on an outside of the vitreous silica crucible; a first polarizer disposed between the light source and the outer surface of the vitreous silica crucible wall; a first quarter-wave plate disposed between the first polarizer and the outer surface of the vitreous silica crucible wall; a CCD camera disposed inside of the vitreous silica crucible; a camera control mechanism configured to control a photographing direction of the CCD camera; a second polarizer disposed between the CCD camera and the inner surface of the vitreous silica crucible wall; and a second quarter-wave plate disposed between the camera and the inner surface of the vitreous silica crucible wall with an optical axis inclined 90 degrees with respect to the first quarter-wave plate. The camera color-photographs the light which is emitted from the light source and passes through the first polarizer, the first quarter-wave plate, the vitreous silica crucible wall, the second quarter-wave plate, and the second polarizer.

According to the present invention, the light coming from the light source is converted into a linearly polarized light at the first polarizer. Further, it is converted into a circularly polarized light at the quarter-wave plate and then irradiates the crucible wall so as to be able to measure the crucible's distortion. For example, sometimes a light of transverse wave cannot pass through the opaque layer due to influence of the bubbles; and a light of longitudinal wave cannot pass through the opaque layer due to influence of the bubbles. However, as for circularly polarized light, it will not be influenced by the bubbles so much and it can pass through the opaque outer layer. The transmitted light can pass through the second quarter-wave plate inclined 90 degrees with respect to the first quarter-wave plate and the second polarizer and then be photographed at the CCD camera. Therefore, it is possible to photograph the transmitted light reflecting the vitreous silica crucible's distortion.

In the present invention, preferably the second quarter-wave plate is alternatively disposed between the second polarizer and the inner side of vitreous silica crucible wall. According to such configuration, since the distortion in the silica glass appears as a change of color, it is easy to recognize distortion distribution.

In the present invention, the second quarter-wave plate may be alternatively disposed between the camera and the second polarizer. According to such configuration, since the distortion in the silica glass appears as black and white pattern instead of a color pattern, it is easy to recognize distortion distribution.

In the present invention, the first polarizer includes a third polarizer covering the entire height direction of the vitreous silica crucible, and a fourth polarizer covering the entire bottom portion of the vitreous silica crucible. The first quarter-wave plate preferably includes a third quarter-wave plate covering the entire height direction of the vitreous silica crucible and a fourth quarter-wave plate covering the entire bottom portion of the vitreous silica crucible. If the first polarizer and the first quarter-wave plate are small in size, every time the camera's photographing position changes, their positions will also need to be changed, resulting in a long measuring time for each crucible. In addition, there is also a problem that the measurement results may be different due to a subtle change of distance, angle, and so on, between the camera and the optical components when photographing. However, through the use of a large polarizer and quarter-wave plate, there is no need of changing positions for each photograph. In addition, through fixing the polarizer and the quarter-wave plate, the variation in measurement results caused by position adjustment can be suppressed.

In the present invention, the light source preferably includes: a plurality of first LED lights which are arranged at a predetermined interval along the height direction of the vitreous silica crucible and irradiate the side portion of the vitreous silica crucible; and a plurality of second LED lights which are arranged at a predetermined interval along the radial direction of the vitreous silica crucible and irradiate the bottom portion of the vitreous silica crucible. In the case of using one LED light as the light source, every time the camera's photographing position changes, the position of the LED light will also need to be changed, resulting in a long measuring time for each crucible. In addition, there is also a problem that the measurement results may be different due to a subtle change of distance, angle, and so on, between the camera and the light source when photographing. However, through the use of a plurality of LED lights, there is no need of changing positions for each photograph. In addition, through fixing the LED lights, the variation in measurement results caused by position adjustment can be suppressed.

In the present invention, in the camera control mechanism, it is preferable to continuously conduct photographing while moving the camera's photographing direction in one direction along the height direction of the vitreous silica crucible. According to the structure, it is possible to measure the distortion in the entire height direction of the crucible, i.e. the entire region from the crucible's upper rim to the bottom portion so as to objectively determine the distortion distribution in the crucible's height direction.

In the present invention, preferably the camera control mechanism alternatively makes the photographing direction of the camera move along a circumferential direction of the vitreous silica crucible so as to photograph the entire inner circumferential surface of the vitreous silica crucible. Alternatively, the position of the camera may be fixed and the vitreous silica crucible is rotated so as to photograph the entire inner circumferential surface of the vitreous silica crucible. According to this structure, it is possible to recognize the entire distortion distribution of the crucible at a glance so as to evaluate the reliability easily.

Further, the vitreous silica crucible according to the present invention used to pull up silicon single crystal includes: a cylindrical straight body portion; a corner portion formed at a lower end of the straight body portion; a bottom portion connected with the straight body portion via the corner portion; an opaque outer layer constituting an outer side of the crucible and enclosing bubbles therein; and a transparent inner layer, which constitutes an inner side of the crucible and from which bubbles are removed. The residual distortion's distribution obtained by measuring the vitreous silica crucible's inner surface in a non-destructed state has an optical path difference (retardation value) which is 130 nm or less. According to the present invention, it is possible to significantly reduce the probability of a crucible's cracking during material filling operation and to provide a highly reliable vitreous silica crucible.

Effects of the Invention

According to the present invention, it is possible to provide a distortion-measuring apparatus for vitreous silica crucible which can measure a distortion distribution of the entire vitreous silica crucible in a non-destructive way. In addition, according to the present invention, it is possible to provide a vitreous silica crucible which has a residual distortion distribution specified by the above-mentioned distortion-measuring apparatus and does not crack easily when filling material.

BRIEF DESCRIPTION OF THE DRAWINGS

FIG. 1 is a side view drawing schematically showing the structure of a vitreous silica crucible's distortion-measuring apparatus according to Embodiment 1 of the present invention.

FIG. 2 is a plan view drawing schematically showing the structure of the distortion-measuring apparatus in FIG. 1.

FIG. 3 is a schematic drawing explaining an example of the measurement principle of the distortion-measuring apparatus.

FIG. 4 is a drawing schematically showing the structure of a vitreous silica crucible's distortion-measuring apparatus according to Embodiment 2 of the present invention, wherein (a) is a plan view, (b) is a cross-sectional view.

FIG. 5 is a drawing schematically showing the structure of a vitreous silica crucible's distortion-measuring apparatus according to Embodiment 3 of the present invention, wherein (a) is a plan view, (b) is a cross-sectional view.

FIG. 6 is a drawing schematically showing the structure of a vitreous silica crucible's distortion-measuring apparatus according to Embodiment 4 of the present invention.

FIG. 7 is a drawing schematically showing the structure of a vitreous silica crucible's distortion-measuring apparatus according to Embodiment 5 of the present invention.

FIG. 8 is a drawing schematically showing the structure of a vitreous silica crucible's distortion-measuring apparatus according to Embodiment 6 of the present invention.

FIG. 9 is a drawing schematically showing the structure of a vitreous silica crucible's distortion-measuring apparatus according to Embodiment 7 of the present invention, and especially is a view schematically showing another example of the measurement principle shown in FIG. 3.

FIG. 10 is a picture showing measurement results of the vitreous silica crucible's distortion distribution, wherein (a) is a photographic image of a common crucible; (b) is a photographic image a re-arc crucible; and (c) is a photographic image of an annealed crucible.

MODE FOR CARRYING OUT THE INVENTION

Hereinafter, preferred embodiments according to the present invention are described in detail with reference to the accompanied drawings.

FIG. 1 is a side view schematically showing the structure of a distortion-measuring apparatus for a vitreous silica crucible according to Embodiment 1 of the present invention. FIG. 2 is a plan view schematically showing the structure of the distortion-measuring apparatus in FIG. 1.

As shown in FIG. 1 and FIG. 2, the distortion-measuring apparatus 10A according to this embodiment includes: a light source 11 disposed on the outside of the vitreous silica crucible 1, a first polarizer 12 disposed between the light source 11 and the outer surface of the vitreous silica crucible 1 wall, a first quarter-wave plate 13 disposed between the first polarizer 12 and the outer surface of the vitreous silica crucible 1 wall, a CCD camera 14 disposed inside of the vitreous silica crucible 1, a camera control mechanism 15 configured to control a photographing direction of the CCD camera 14, a second polarizer 16 disposed between the CCD camera 14 and the inner surface of the vitreous silica crucible 1 wall, and a second quarter-wave plate 17 disposed between the second polarizer 16 and the inner surface of the vitreous silica crucible 1 wall with an optical axis inclined 90 degrees with respect to the first quarter-wave plate 13.

The vitreous silica crucible 1 is mainly used to pull up silicon single crystal. The crucible 1 includes: a cylindrical straight body portion 1a, a corner portion 1c formed at the lower end of the straight body portion, and a bottom portion 1b connected to the straight body portion via the corner portion. The crucible wall has different thickness at different positions. The thickness is preferably more than 10 mm. Also, the wall of the vitreous silica crucible 1 includes: an opaque outer layer 2 constituting an outer layer and enclosing a plurality of bubbles, and a transparent inner layer 3, which constitutes an inner side of the crucible and from which bubbles are removed. The plurality of bubbles in the outer layer 2 make the light scatter and make the polarization direction variable, resulting in difficulty observing the distortion (birefringence phase difference) by using transmitted light. However, by the distortion-measuring apparatus 10A of the present invention, it is possible to measure the distortion of the vitreous silica crucible 1.

The light source 11 includes: a first LED light group 11a illuminating the side portion of the vitreous silica crucible 1 and a second LED light group 11b illuminating the bottom portion of the vitreous silica crucible 1. The first LED light group 11a has a plurality of LED lights which are arranged at predetermined intervals along the height direction of the vitreous silica crucible 1. The second LED light group 11b has a plurality of LED lights which are arranged at predetermined intervals along the radial direction of the vitreous silica crucible 1.

Output light from each LED is preferably a light source of combined single-wavelength lights such as blue light (a central wavelength of about 450 nm), green light (a central wavelength of about 520 nm), and red light (a central wavelength of about 660 nm) in the visible wavelength range. Additionally, the wavelength range of the green light is 490-580 nm. If using an output light with such wavelength range, the glass's distortion can be clearly represented as color unevenness in the photographic image. It should be noted that it is preferable to dispose the distortion-measuring apparatus 10A in a dark room in order to prevent variation of the distortion distribution measurement results caused by the influence of light other than the light source 11.

The first polarizer 12 is structured by a third polarizer 12a which covers the entire height direction of the vitreous silica crucible 1 and a fourth polarizer 12b which covers the entire bottom portion of the vitreous silica crucible 1. In addition, the first quarter-wave plate 13 is structured by a third quarter-wave plate 13a which covers the entire height direction of the vitreous silica crucible 1 and a fourth quarter-wave plate 13b which covers the entire bottom portion of the vitreous silica crucible 1. The third polarizer 12a and the fourth polarizer 12b as well as the third quarter-wave plate 13a and the fourth quarter-wave plate 13b are fixed to fixed positions.

If the first polarizer 12 and the first quarter-wave plate 13 are small in size, every time the CCD camera 14's photographing position is changed, these optical components' positions will also need to be changed, which causes a problem of long measurement time for each crucible. In addition, there is also a problem that the measurement results may be different due to a subtle change of distance, angle, and so on, between the CCD camera 14 and the optical components when photographing. However, through the use of a large polarizer and quarter-wave plate, there is no need of changing position for each photograph. In addition, through fixing the polarizer and the quarter-wave plate, the variation in measurement results caused by position adjustment can be suppressed.

The second polarizer 16 and the second quarter-wave plate 17 are used as additional lenses to be directly mounted on the CCD camera 14 and move together with the CCD camera 14. They may be any size as long as they can cover the CCD camera 14's photographing range but do not need to cover a wide range like the first polarizer 12 and the first quarter-wave plate 13.

The CCD camera 14 photographs the inner surface of the crucible. It is necessary for the CCD camera 14 to be able to conduct color photographing because the vitreous silica crucible's distortion distribution is obtained as a variation in color. The CCD camera 14 receives light which is emitted from the light source 11 and passes through the first polarizer 12, the first quarter-wave plate 13, the wall of the vitreous silica crucible 1, the second quarter-wave plate 17, and the second polarizer 16. The image data photographed by the CCD camera 14 is captured by a computer not shown in figures, and displayed on a display after predetermined image processing.

The camera control mechanism 15 has a tilt-angle adjustment function for making the CCD camera 14 rotate in a vertical plane (first reference plane) including the crucible's central axis Z as shown by arrow D1, and a height adjustment function for making the CCD camera 14 move in the direction of the crucible's central axis Z as shown by arrow D2. As a result, the camera control mechanism 15 enables the CCD camera 14's photographing direction to move along the vitreous silica crucible 1's height direction. The CCD camera 14 photographs the crucible's inner surface while moving at a range from the crucible's upper rim to the center of the bottom. That is to say, the distortion distribution in the crucible's height direction can be measured.

In addition, the camera control mechanism 15 has a pan-angle adjustment function which makes the CCD camera 14 rotate in the horizontal plane (second reference plane) perpendicular to the crucible's central axis as shown by arrow D3. As a result, the camera control mechanism 15 enables the CCD camera 14's photographing direction to move along a horizontal direction so that the CCD camera 14 can photograph the vitreous silica crucible 1 over its entire circumference. That is to say, the following process is repeated over the entire circumference: after measuring the distortion distribution in the height direction, the camera control mechanism 15 moving the photographing line to an adjacent circumferential direction and measuring the distortion distribution in the height direction once again. Alternatively, the following process may be repeated over the entire circumference: after measuring the distortion distribution in the circumferential direction, moving the photographing line to an adjacent height direction and measuring the distortion distribution in the circumferential direction once again. According to this, the distortion distribution of the whole crucible can be measured. Therefore, it is possible to know the distortion distribution of the entire crucible at a glance from the photographic images, and it is easy to evaluate reliability of the crucible.

FIG. 3 is a schematic drawing for explaining an example of the measurement principle of the distortion-measuring apparatus 10A.

As shown in FIG. 3, a natural polarized light coming from the light source 11 is converted into linearly polarized light by passing through the first polarizer 12 and further converted into circularly polarized light by passing through the first quarter-wave plate 13. The circularly polarized light passes through the wall of the vitreous silica crucible 1 and furthermore passes through the second quarter-wave plate 17 and the second polarizer 16.

If the linearly polarized light coming from the first polarizer 12 irradiates the wall of the vitreous silica crucible 1 without any change, the plurality of bubbles of the crucible in the outer layer 2 will make the light scatter, which results in a difficulty of obtaining enough transmitted light and observing the distortion (birefringence phase difference). However, according to the distortion-measuring apparatus 10A of the present invention, the vitreous silica crucible 1 is irradiated after converting the linearly polarized light into circularly polarized light. Therefore, it is still possible to obtain an effective amount of light required even if the light is scattered due to bubbles' influence, and it is possible to measure the distortion of the vitreous silica crucible.

The circularly polarized light passing through the wall of the vitreous silica crucible 1 is converted into linearly polarized light by passing through the second quarter-wave plate 17 and then passes through the second polarizer 16 and is captured by the CCD camera 14. In the photographic images of the CCD camera 14, the residual distortion of the vitreous silica crucible 1 appears. The vitreous silica crucible having distortion shows birefringence. The extent of the distortion is determined based on the polarization photo. A yellow-green color, which is the wavelength color of the light source 11, appears at positions where there is no distortion but compression distortion appears as blue color and tension distortion appears as red color. In this way, the distortion in the silica glass appears as color change so it is easy to determine the distortion distribution.

As described above, the distortion-measuring apparatus for the vitreous silica crucible according to the present embodiment converts a linearly polarized light into circularly polarized light and then irradiates the crucible's wall so as to be able to suppress the influence of the plurality of bubbles enclosed in the crucible's outer layer 2 and make light pass through. As a result, it is possible to observe the distortion in the vitreous silica crucible. Therefore, it is possible to measure the vitreous silica crucible's distortion non-destructively and correctly measure the distortion distribution of the entire crucible.

The vitreous silica crucible 1, not as a fragment partially cut out but in a non-destructed state where the entire circumference is restrained, has a residual distortion's distribution obtained by measuring the vitreous silica crucible's inner surface, which preferably has an optical path difference (retardation value) of 130 nm or less. The residual distortion in the silica glass mentioned here is a result of measuring birefringence phase difference from the vitreous silica crucible 1's inner surface and is a sum of the residual compressive stress and the residual tensile stress inside the silica glass. If the compressive stress and the tensile stress against a thickness direction of the crucible's wall exist to the same extent, the sum of residual stress will become zero and the optical path difference will also become almost zero. These compressive residual stress and tensile residual stress will not become a reason for causing the crucible's distortion because they offset each other when the crucible is heated in the single crystal pulling-up process.

In the vitreous silica crucible 1, it is possible to significantly reduce the probability of crucible's cracking during material filling operation and increase the reliability of the vitreous silica crucible. The size of such vitreous silica crucible's residual distortion is able to be measured for the first time by using the distortion-measuring apparatus. The distortion-measuring apparatus according to the present invention has a great effect on quality determination for the vitreous silica crucible.

In the above embodiment, the first polarizer 12 and the first quarter-wave plate 13 are completely fixed. However, the first polarizer 12 and the first quarter-wave plate 13 may be structured to move according to the photographing position of the CCD camera 14.

FIG. 4 is a drawing schematically showing the structure of a vitreous silica crucible's distortion-measuring apparatus according to Embodiment 2 of the present invention, wherein (a) is a plan view, (b) is a cross-sectional view.

As shown in (a) and (b) in FIG. 4, the point of the distortion-measuring apparatus 10B in the present embodiment is that the light source 11, the first polarizer 12, and the first quarter-wave plate 13 are disposed only on the optical axis of the CCD camera 14 in plan view, instead of disposing it all around the circumference of the crucible. In a situation of photographing the entire circumference, the crucible is rotated and the CCD camera 14 is scanned in a circumferential direction of the crucible.

As shown in (b) in FIG. 4, the first polarizer 12 and the first quarter-wave plate 13 are disposed only on the optical axis of the CCD camera 14 not only in a circumferential direction but also in a height direction. Therefore, a platform supporting the crucible has both rotation function and lift function. It is preferable to make the crucible move in both a circumferential direction and height direction according to the photographing position of the CCD camera 14. Even with such configuration, the distortion distribution of the entire crucible can be measured which is similar to Embodiment 1. Therefore, it is possible to know the distortion distribution of the entire crucible at a glance from the photographic images, and it is easy to evaluate reliability of the crucible.

In the above Embodiment 1, the first polarizer 12 and the first quarter-wave plate 13 are completely fixed. However, for example, the first polarizer 12 and the first quarter-wave plate 13 may cover both of height direction and radial direction of the crucible entirely, but only cover a point of photographing position of the CCD camera 14 in a circumferential direction, and move along the circumferential direction of the crucible according to the photographing position.

FIG. 5 is a drawing schematically showing the structure of a vitreous silica crucible's distortion-measuring apparatus according to Embodiment 3 of the present invention, wherein (a) is a plan view, (b) is a cross-sectional view.

As shown in (a) and (b) in FIG. 5, the distortion-measuring apparatus 10C in the present embodiment is disposed such that the light source 11, the first polarizer 12, and the first quarter-wave plate 13 are disposed on one point of the optical axis of the CCD camera 14 with reference to the circumferential direction of the crucible; however, it covers the entire side surface and the entire bottom surface with reference to the height direction and the radial direction of the crucible. The third polarizer 12a and the third quarter-wave plate 13a are formed by a belt-like member which is elongated along the height direction. The fourth polarizer 12b and the fourth quarter-wave plate 13b are formed by a belt-like member which is elongated along the horizontal direction.

When photographing the entire circumference of the crucible, similar to Embodiment 2, the crucible is rotated and the CCD camera 14 scans in the circumferential direction of the crucible. In addition, when measuring in the height direction and the radial direction of the crucible, the CCD camera 14 is moved for measuring. Even with such configuration, similar to Embodiment 1, it is also possible to measure the distortion distribution of the entire crucible. Therefore, it is possible to know the distortion distribution of the entire crucible at a glance from the photographic images, and it is easy to evaluate reliability of the crucible.

FIG. 6 is a drawing schematically showing the structure of a vitreous silica crucible's distortion-measuring apparatus according to Embodiment 4 of the present invention.

As shown in FIG. 6, the distortion-measuring apparatus 10D in the present embodiment measures the vitreous silica crucible 1 in a state facing laterally. That is to say, the crucible is set so that the opening portion faces a horizontal direction. The light source 11a which is used for illuminating the crucible's bottom is disposed next to the crucible. The light source 11b which is used for illuminating the crucible's side portion is disposed at the bottom of the crucible. The light source 11b which is used for illuminating the crucible's side portion may also be disposed on top of the crucible. The other configurations are the same as Embodiment 3 when measuring along the circumferential direction of the crucible, the CCD camera 14 is fixed and the crucible is rotated.

According to the present embodiment, similar to the above embodiment, the distortion distribution of the entire crucible can also be measured. Therefore, it is possible to know the distortion distribution of the whole crucible at a glance from the photographic images, and it is easy to evaluate reliability of the crucible.

FIG. 7 is a drawing schematically showing the structure of a vitreous silica crucible's distortion-measuring apparatus according to Embodiment 5 of the present invention.

As shown in FIG. 7, the distortion-measuring apparatus 10E of the present embodiment measures the vitreous silica crucible 1 in a state facing downward. That is to say, the crucible is disposed on, for example, a rotary table in a state where the opening portion faces downwards. The light source 11a which is used for illuminating the crucible's bottom is disposed on top of the crucible. The light source 11b which is used for illuminating the crucible's side portion is disposed next to the crucible. The configuration is the same as Embodiment 3 when measuring along the circumferential direction of the crucible, the CCD camera 14 is fixed and the crucible is rotated.

According to the present embodiment, similar to the above embodiment, the distortion distribution of the entire crucible can also be measured. Therefore, it is possible to know the distortion distribution of the entire crucible at a glance from the photographic images, and it is easy to evaluate reliability of the crucible.

FIG. 8 is a drawing schematically showing the structure of a vitreous silica crucible's distortion-measuring apparatus according to Embodiment 6 of the present invention.

As shown in FIG. 8, the distortion-measuring apparatus 10F of the present embodiment disposes the CCD camera 14, the second polarizer 16, and the second quarter-wave plate 17 at an outer side instead of inner side of the crucible. The crucible is set so that the opening portion faces upward. The light source 11a illuminating the bottom portion of the crucible is disposed at the bottom of the crucible. The light source 11b illuminating the side portion of the crucible is disposed next to the crucible. The other configurations are the same as Embodiment 3 when measuring along the circumferential direction of the crucible, the CCD camera 14 is fixed and the crucible is rotated so as to conduct scanning by the CCD camera in the circumferential direction.

According to the present embodiment, similar to the above embodiment, the distortion distribution of the entire crucible can also be measured. Therefore, it is possible to know the distortion distribution of the entire crucible at a glance from the photographic images, and it is easy to evaluate reliability of the crucible.

FIG. 9 is a vitreous silica crucible's distortion-measuring apparatus according to Embodiment 7 of the present invention, and especially it is a drawing schematically showing another example of the measurement principle shown in FIG. 3.

As shown in FIG. 9, the distortion-measuring apparatus 10G exchanges the positions of the second quarter-wave plate 17 and the second polarizer 16 of FIG. 3. The light which comes from the light source 11, passes through the first polarizer 12, the first quarter-wave plate 13, and the vitreous silica crucible wall passes through the second polarizer 16, then passes through the second quarter-wave plate 17, and enters the CCD camera 14. There appears residual distortion in the silica glass in the image photographed by the CCD camera 14 but this residual distortion appears as a black and white pattern instead of a color pattern. Therefore, it is possible to determine the distortion distribution based on the same measurement principle as in the FIG. 3.

Preferable embodiments of the present invention are explained above, but the present invention is not limited to the above embodiments. It is possible to have various modifications without departing from the scope of the present invention, and it is needless to say that they are within the scope of the present invention.

For example, in the above embodiment, the first polarizer 12 and the first quarter-wave plate 13 correspond to the side components of the crucible (the third polarizer 12a and the third quarter-wave plate 13a) and the bottom components of the crucible (the fourth polarizer 12b and the fourth quarter-wave plate 13b), respectively, and are separated. However, they may also be a single component integrally formed along the outline of the crucible.

EXAMPLES

A non-destructive measurement of the distortion distribution of the vitreous silica crucible was conducted by the distortion-measuring apparatus of the present invention. There are three kinds of vitreous silica crucibles as measurement objects, which are: a common vitreous silica crucible formed by an arc fusing method (common crucible), a re-arc crucible formed by fusing the common crucible once again, and an annealed crucible by annealing the common crucible. As the annealing conditions, the crucible is heated for 1 hour at 1100 degrees and then cooled to room temperature. The results are shown in FIG. 10. (a) is the photographed image of the common crucible, (b) is the photographed image of the re-arc crucible, and (c) is the photographed image of the annealed crucible in FIG. 10. The results of measuring the three kinds of crucibles from the inner surface are shown in FIG. 10.

As shown in FIG. 10, with regard to the common crucible in (a) and the annealed crucible in (c), there is very little distortion; and with regard to the re-arc crucible in (b), black stripes at an upper end of the rim and dense, dilute porphyritic distinctive distortion distribution at the bottom can be seen. The re-arc crucible's distortion distribution tends to be similar to the situation measured by a conventional method.

DESCRIPTION OF THE SYMBOLS

1 Vitreous silica crucible
2 Crucible outer layer
3 Crucible inner layer
10A-10G Distortion-measuring apparatus
11 Light source
11a First LED light group
11b Second LED light group
12 First polarizer
12a Third polarizer
12b Fourth polarizer
13 First wave plate
13a Third wave plate
13b Fourth wave plate
14 CCD camera
15 Camera control mechanism
16 Second polarizer
17 Second wave plate

What is claimed is:
1. A distortion-measuring apparatus of a vitreous silica crucible, in which the crucible includes an opaque outer layer containing a plurality of bubbles and a transparent inner layer with bubbles removed, the distortion-measuring apparatus comprising:
a light source disposed outside of the vitreous silica crucible;
a first polarizer disposed between the light source and an outer surface of the vitreous silica crucible's wall;
a first quarter-wave plate disposed between the first polarizer and the outer surface of the vitreous silica crucible wall;
a camera disposed inside of the vitreous silica crucible;
a camera control mechanism configured to control a photographing direction of the camera;
a second polarizer disposed between the camera and an inner surface of the vitreous silica crucible wall; and
a second quarter-wave plate disposed between the camera and the inner surface of the vitreous silica crucible wall with an optical axis inclined 90 degrees with respect to the first quarter-wave plate;
wherein the camera conducts color photographing of light which is emitted from the light source and passes through the first polarizer, the first quarter-wave plate, the wall of the vitreous silica crucible, the second quarter-wave plate, and the second polarizer.

2. The distortion-measuring apparatus according to claim 1, wherein the second quarter-wave plate is disposed between the second polarizer and an inner surface of the vitreous silica crucible wall.

3. The distortion-measuring apparatus according to claim 2, wherein the first polarizer comprises: a third polarizer covering the entire vitreous silica crucible in a height direction, and a fourth polarizer covering the entire bottom of the vitreous silica crucible;
the first quarter-wave plate comprises: a third quarter-wave plate covering the entire vitreous silica crucible in a height direction, and a fourth quarter-wave plate covering the entire bottom of the vitreous silica crucible.

4. The distortion-measuring apparatus according to claim 3, wherein the light source comprises: a plurality of first LED lights which are arranged at certain intervals along the height direction of the vitreous silica crucible and illuminate the side portion of the vitreous silica crucible; and
a plurality of second LED lights which are arranged at certain intervals along the radical direction of the vitreous silica crucible and illuminate the bottom portion of the vitreous silica crucible.

5. The distortion-measuring apparatus according to claim 2, wherein the camera control mechanism makes the camera perform continuous photographing while making the photographing direction of the camera move in one direction along the height direction of the vitreous silica crucible.

6. The distortion-measuring apparatus according to claim 5, wherein the camera control mechanism makes the photographing direction of the camera move along the circumferential direction of the vitreous silica crucible so as to perform photographing the entire inner circumferential surface of the vitreous silica crucible.

7. The distortion-measuring apparatus according to claim 5, wherein the camera's position is fixed and the vitreous silica crucible is rotated so as to photograph the entire inner circumferential surface of the vitreous silica crucible.

8. The distortion-measuring apparatus according to claim 1, wherein the second quarter-wave plate is disposed between the camera and the second polarizer.

9. The distortion-measuring apparatus according to claim 8, wherein the first polarizer comprises: a third polarizer covering the entire vitreous silica crucible in a height direction, and a fourth polarizer covering the entire bottom of the vitreous silica crucible;
the first quarter-wave plate comprises: a third quarter-wave plate covering the entire vitreous silica crucible in a height direction, and a fourth quarter-wave plate covering the entire bottom of the vitreous silica crucible.

10. The distortion-measuring apparatus according to claim 9, wherein the light source comprises: a plurality of first LED lights which are arranged at certain intervals along the height direction of the vitreous silica crucible and illuminate the side portion of the vitreous silica crucible; and
a plurality of second LED lights which are arranged at certain intervals along the radical direction of the vitreous silica crucible and illuminate the bottom portion of the vitreous silica crucible.

11. The distortion-measuring apparatus according to claim 8, wherein the camera control mechanism makes the camera perform continuous photographing while making the photographing direction of the camera move in one direction along the height direction of the vitreous silica crucible.

12. The distortion-measuring apparatus according to claim 11, wherein the camera control mechanism makes the photographing direction of the camera move along the circumferential direction of the vitreous silica crucible so as to perform photographing the entire inner circumferential surface of the vitreous silica crucible.

13. The distortion-measuring apparatus according to claim 11, wherein the camera's position is fixed and the vitreous silica crucible is rotated so as to photograph the entire inner circumferential surface of the vitreous silica crucible.

14. The distortion-measuring apparatus according to claim 1, wherein the first polarizer comprises: a third polarizer covering the entire vitreous silica crucible in a height direction, and a fourth polarizer covering the entire bottom of the vitreous silica crucible;
the first quarter-wave plate comprises: a third quarter-wave plate covering the entire vitreous silica crucible in a height direction, and a fourth quarter-wave plate covering the entire bottom of the vitreous silica crucible.

15. The distortion-measuring apparatus according to claim 14, wherein the light source comprises: a plurality of first LED lights which are arranged at certain intervals along the height direction of the vitreous silica crucible and illuminate the side portion of the vitreous silica crucible; and
a plurality of second LED lights which are arranged at certain intervals along the radical direction of the vitreous silica crucible and illuminate the bottom portion of the vitreous silica crucible.

16. The distortion-measuring apparatus according to claim 1, wherein the camera control mechanism makes the camera perform continuous photographing while making the photographing direction of the camera move in one direction along the height direction of the vitreous silica crucible.

17. The distortion-measuring apparatus according to claim 16, wherein the camera control mechanism makes the photographing direction of the camera move along the circumferential direction of the vitreous silica crucible so as to perform photographing the entire inner circumferential surface of the vitreous silica crucible.

18. The distortion-measuring apparatus according to claim 16, wherein the camera's position is fixed and the vitreous silica crucible is rotated so as to photograph the entire inner circumferential surface of the vitreous silica crucible.

* * * * *